United States Patent [19]

Sletzinger et al.

[11] Patent Number: 4,620,025

[45] Date of Patent: Oct. 28, 1986

[54] PROCESS FOR THE PREPARATION OF BIPHENYL INTERMEDIATES

[75] Inventors: Meyer Sletzinger, North Plainfield; Thomas R. Verhoeven, Cranford, both of N.J.

[73] Assignee: Merck & Co., Inc., Rahway, N.J.

[21] Appl. No.: 637,081

[22] Filed: Aug. 1, 1984

[51] Int. Cl.$^4$ .................. C07C 121/70; C07C 69/533; C07C 43/303

[52] U.S. Cl. .................. 558/401; 560/59; 560/102; 568/592

[58] Field of Search ........... 260/465 G, 465 F, 465 R, 260/465 K; 560/59, 102; 568/592; 558/401

[56] References Cited

U.S. PATENT DOCUMENTS 4,322,563  3/1982  Hoffman ........................... 568/425
4,375,475  3/1983  Willard et al. ..................... 424/279

OTHER PUBLICATIONS

Negishi et al., J. Org. Chem., vol. 42, pp. 1821–1823 (1977).
Meyers et al., J. Org. Chem., vol. 46, pp. 3881–3886, (1981).

*Primary Examiner*—Dolph H. Torrence
*Attorney, Agent, or Firm*—Joseph F. DiPrima; Michael C. Sudol, Jr.

[57] ABSTRACT

A novel process for the preparation of intermediates in the totally synthetic antihypercholesterolemic agents, 6-[2-[1,1'-biphenyl]-2-yl-ethenyl] pyranones, involving a highly efficient nickel catalyzed aryl cross-coupling reaction is disclosed.

7 Claims, No Drawings

PROCESS FOR THE PREPARATION OF BIPHENYL INTERMEDIATES

BACKGROUND OF THE INVENTION

Totally synthetic antihypercholesterolemic and hypolipemic compounds represented by the following general structural Formula (I):

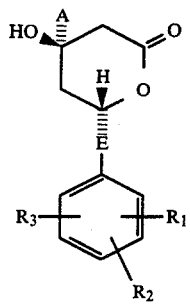

and specific derivatives thereof, all of which being the enantiomers having a 4(R) configuration in the tetrahydropyran moiety of the trans racemate shown in Formula (I) are disclosed in U.S. Pat. No. 4,375,475. One class of especially preferred compounds are those compounds of the Formula (I) wherein A is hydrogen, E is —CH=CH— and $R_3$ is a substituted phenyl radical in the 6-position. The synthesis of these 6-[2-[1,1'-biphenyl]-2-yl-ethenyl]pyranones disclosed in U.S. Pat. No. 4,375,475 proceeds through an intermediate benzaldehyde of the Formula (II)

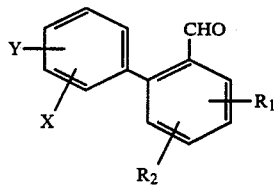

wherein $R_1$, $R_2$, X and Y are described therein, and an intermediate aryl-2-propenal of the Formula (III)

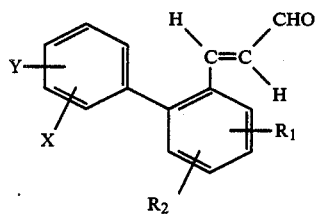

wherein $R_1$, $R_2$, X and Y are described therein.

The intermediate benzaldehyde compounds of the Formula (II) which are 3,5-dichloro-4'-fluoro-1,1'-biphenyl-1-carboxaldehyde; 3,5-dimethyl-4'-fluoro-1,1'-biphenyl-2-carboxaldehyde; 3,3',5-trimethyl-4'-fluoro-1,1'-biphenyl-2-carboxaldehyde; and 3,3',5,5'-tetramethyl-1,1'-biphenyl-2-carboxaldehyde are claimed in U.S. Pat. No. 4,322,563. A process for the preparation of these compounds is also disclosed therein.

SUMMARY OF THE INVENTION

This invention relates to a novel process for the preparation of intermediates in the totally synthetic antihypercholesterolemic agents, 6-[2-[1,1'-biphenyl]-2-yl-ethenyl]pyranones. The novel process involves a highly efficient nickel-catalyzed aryl cross-coupling reaction which utilizes commercially available reagents and starting materials and affords products which are easily isolated and purified.

DETAILED DESCRIPTION OF THE INVENTION

A process for the preparation of a compound represented by the following general Formula (IV)

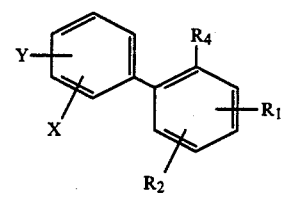

wherein:
$R_1$ and $R_2$ independently are:
 (1) chloro;
 (2) fluoro; or
 (3) $C_{1-4}$ alkyl;
$R_4$ is
 (1) —CN;
 (2) —CO$_2$R$_5$;
 (3) —CH(OR$_5$)$_2$;
 (4) —CH=CHCN;
 (5) —CH=CHCO$_2$R$_5$; or
 (6) —CH=CHCH(OR$_5$)$_2$ in which $R_5$ is $C_{1-4}$ alkyl; and
X and Y independently are:
 (1) hydrogen;
 (2) chloro;
 (3) fluoro;
 (4) $C_{1-4}$ alkyl; or
 (5) $C_{1-4}$ alkoxy
comprises reacting a compound of the Formula (V):

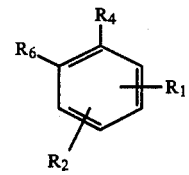

wherein $R_1$, $R_2$ and $R_4$ are defined above, and $R_6$ is halogen, such as chloro, bromo or iodo, with a compound of the Formula (VI)

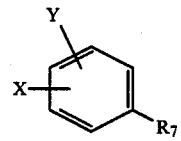

wherein X and Y are defined above,
and $R_7$ is
 (1) ZnR$_8$;
 (2) MgR$_8$;
 (3) CdR$_8$; or
 (4) Li in which $R_8$ is halogen or a radical represented by the following formula:

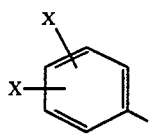

wherein X and Y are defined above, in the presence of a nickel catalyst.

The intermediate benzaldehyde compounds of the Formula (II) are readily prepared by (1) the reduction of the appropriate products the nickel-catalyzed aryl cross-coupling reaction of this invention, the compounds of the Formula (IV) wherein $R_4$ is —CN or —$CO_2R_5$ or (2) the acid hydrolysis of the compounds of formula (IV) wherein $R_4$ is —$CH(OR_5)_2$. Similarly, the intermediate aryl-2-propenal compounds of the Formula (III) are readily prepared by (1) the reduction of the compounds of Formula (IV) wherein $R_4$ is —CH=$CHCO_2R_5$ or —CH=CHCN or (2) the acid hydrolysis of the compounds of the formula (IV) wherein $R_4$ is —CH=$CHCH(OR_5)_2$.

In a preferred embodiment, the compounds prepared by the process of this invention are those compounds of the Formula (IV) wherein $R_1$ and $R_2$ are in the 3- and 5-positions and independently are chloro, fluoro or methyl; and X and Y independently are chloro, fluoro, methyl or methoxy.

In a most preferred embodiment the compounds prepared by the process of this invention are:
(1) 4'-fluoro-3,3',5-trimethyl-[1,1'-biphenyl]-2-carbonitrile;
(2) E-3-(4'-fluoro-3,3',5-trimethyl-[1,1'-biphenyl]-2-yl)-2-propenoic acid nitrile;
(3) 4'-fluoro-3,3',5-trimethyl-[1,1'-biphenyl]-2-carboxaldehyde;
(4) E-3-(4'-fluoro-3,3',5-trimethyl-[1,1'-biphenyl]-2-yl)-2-propenal; and
(5) Methyl E-3-(4'-fluoro-3,3',5-trimethyl-[1,1'-biphenyl]-2-yl)-2-propenoate.

The nickel-catalyzed aryl cross-coupling reaction of this novel process is conducted at a temperature between 10° and 65° C., preferably at 20°–25° C., for between 0.5 and 6 hours in an inert solvent. Illustrative of such inert solvents are: hydrocarbons, such as hexane, toluene, cyclohexane or the like; and ethers, such as diethyl ether, tetrahydrofuran, dimethoxyethane and the like or mixtures thereof. The preferred solvent is tetrahydrofuran.

The amount of reactants that is employed in the cross-coupling reaction may vary between 0.5 and 1.5 equivalents of the Compound (V) to each equivalent of the Compound (VI). However, equimolar amounts of the reactants are preferred. The compound of the formula (VI) wherein $R_7$ is $ZnR_8$ is a preferred reactant.

The nickel catalysts which are employed in the aryl cross-coupling reaction are organophosphine coordinated nickel dihalide complexes wherein the organophosphine is selected from the group consisting of:
(1) triphenylphosphine;
(2) tri-o-toluylphosphine;
(3) 1,2-bis(diphenylphosphino)ethane;
(4) 1,3-bis(diphenylphosphino)propane;
(5) 1,1'-bis(diphenylphosphino)ferrocene;
and the like and the halide selected from chloride, bromide or iodide. The preferred nickel catalyst is bis(triphenylphosphine) nickel dichloride. Prereduction of the nickel catalyst with diisobutylaluminum hydride prior to its introduction into the reaction mixture may be carried out but is not preferred. The amount of catalyst required in this reaction varies between 0.25 and 10 percent molar percent, with 3 percent preferred.

It should be noted that the organophosphine ligands are critical to avoid undue isomerization of the olefin geometry (i.e. interconversion of the E configuration to the Z configuration) during the cross-coupling reaction when $R_4$ is —CH=CHCN, —CH=$CHCO_2R_5$ or —CH=$CHCH(OR_5)_2$. The mole ratio of organophosphine to nickel may vary between 1 to 4 although the optimum ratio is 2.

The reduction of the compounds of the Formula (IV), wherein $R_4$ is —CN, —$CO_2R_5$, —CH=CHCN or —CH=$CHCO_2R_5$, is conducted at a temperature between —40° and 0° C., preferably at —40° C., for between 0.5 and 4 hours in an inert solvent. Illustrative of such inert solvents are: hydrocarbons, such as hexane, toluene, cyclohexane and the like; halocarbons, such as methylene chloride, ethylene dichloride and the like; ethers, such as, tetrahydrofuran, diethyl ether, dimethoxyethane and the like or mixtures thereof. The preferred solvent is toluene.

The reducing agents which may be employed include diisobutylaluminum hydride, sodium triethoxyaluminum hydride, lithium aluminum hydride, Raney nickel in formic acid or stannous chloride with hydrogen chloride. Preferably diisobutylaluminum hydride is employed. The amount of reducing agent may vary between 1.0 and 2.0 equivalents, with 1.05 equivalents preferred.

The following examples illustrate the present invention and as such are not to be considered as limiting the invention set forth in the claims appended hereto.

EXAMPLE 1

Preparation of 4'-Fluoro-3,3',5-trimethyl-[1,1'-biphenyl]-2-carboxaldehyde (a) 2-Bromo-4,6-dimethylaniline hydrobromide (1a)

A 1 1, 3-necked round-bottom flask, equipped with an overhead stirrer, thermometer, and addition funnel was placed in a heating mantle and charged with 2,4-dimethylaniline (60 g, 0.495 mol), propionic acid (450 ml) and water (2 ml). Rapid stirring was initiated as a solution of bromine (93 g, 0.582 mol) in propionic acid (50 ml) was added over 5 minutes. The resulting slurry was stirred at 85°–90° C. for 40 minutes while monitoring the progress of the reaction by high pressure liquid chromatography (HPLC). After cooling to ambient temperature, ethylene was bubbled through the mixture to discharge the color. After cooling to 10° C. and a 15 minute age, the mixture was filtered. The product was washed with chilled propionic acid (150 ml) then hexane (400 ml) added portionwise. The white to cream colored solid was air dried with final drying accomplished under vacuum. The Compound 1a was obtained as a fine white powder.

(b) 2-Bromo-4,6-dimethylbenzonitrile (1b)

The Compound 1a (14.0 g, 49.8 mmol) was slurried in a solution of water (40 ml) and concentrated hydrochloric acid (6 ml) then cooled to —1° C. A solution of sodium nitrite (3.8 g, 55.0 mmol) in water (15 ml) was added over 15 minutes maintaining an internal temperature of 0° C. After a subsequent 10 minute age, the resulting yellow solution was neutralized by slow addition of a solution of potassium carbonate (2.0 g) in water (5 ml) at 0° C. over a 10 minute period. A cloudy mixture resulted with a pH of 6.5. In a separate vessel, a solution of sodium cyanide (12.8 g, 261 mmol) and cuprous chloride (6.4 g, 64.6 mmol) in water (30 ml) was prepared, toluene (30 ml) was added and the two-phase mixture cooled to 0° C. The diazonium salt mixture was added over 15 minutes to vigorously stirred toluene-/aqueous NaCN-CuCl mixture at 4°–6° C. The mixture was warmed to 20° C. over 1 hour then heated to 50° C. and aged for 5 minutes. The mixture was allowed to recool to 20° C. After filtration, the mixture was diluted with ethyl acetate (125 ml) and the layers separated. The organic phase was washed successively with water (200 ml), 4 N aqueous hydrochloric acid (200 ml), and saturated brine solution (200 ml). The organic phase was treated with activated charcoal (1.4 g), dried over magnesium sulfate, filtered and the solvent removed in vacuo to yield the Compound 1b as an orange solid.

(c) 4'-Fluoro-3,3',5-trimethyl-[1,1'-biphenyl]-2-carbonitrile (1c)

A dry 500 ml, 3-necked round-bottom flask equipped with a thermometer, addition funnel, and condenser was purged with nitrogen then charged with magnesium turnings (6.3 g, 0.265 mol) and sieve-dried tetrahydrofuran (60 ml). A solution of 5-bromo-2-fluorotoluene (33.5 g, 0.177 mol) in tetrahydrofuran (110 ml) was added over 40 minutes maintaining an internal temperature of 50° C. The mixture was allowed to cool to ambient temperature then transferred via cannula to a nitrogen-purged, dry, 500 ml 3-necked round-bottom flask equipped with an overhead stirrer and containing freshly fused zinc chloride (19.35 g, 0.142 mol). An internal temperature of 18° C. was maintained during the addition. A dry, nitrogen purged 50 ml round-bottom flask was charged with dichlorobis(triphenylphosphine)nickel (II) (2.32 g, 0.0035 mol) and dry tetrahydrofuran then cooled to 0° C. A 25% solution of diisobutylaluminum hydride in toluene (4.7 ml) was gradually added allowing the black mixture to warm to 20° C. A portion of the Compound 1b (2 g, 0.0095 mol) was added and the mixture aged 15 minutes at 20° C. After cooling the Grignard solution to 6° C., the nickel catalyst solution was added via cannula. The remaining Compound 1b (28 g, 0.133 mol) was added and the mixture stirred at 20°–25° C. for 2.5 hours. The reaction mixture was diluted with ethyl acetate (200 ml), and washed successively with water, and saturated brine solution. The organic extracts were stirred over activated charcoal (1.4 g) for 15 minutes, dried over sodium sulfate, filtered and the solvent removed in vacuo to yield a yellow solid. The crude product was dissolved in refluxing 85% aqueous ethanol (300 ml), aged at room temperature overnight, cooled to 0° C. then filtered. The filter cake was washed with cold aqueous ethanol and dried yielding the Compound 1c as a yellow solid (mp 98°–100° C.).

(d) 4'-Fluoro-3,3',5-trimethyl-[1,1'-biphenyl]-2-carboxaldehyde

A 250 ml round-bottom flask was charged with toluene (80 ml) and the Compound 1c (30 g, 0.14 mol) and cooled to −40° C. Diisobutylaluminum hydride (98 ml, 0.147 mol, 1.5 molar solution in toluene) was added at −40° C. then aged at that temperature for 1 hour. The solution was added to a rapidly stirred solution of 3 N aqueous hydrochloric acid (700 ml) at 35° C. After stirring overnight the mixture was diluted with toluene (200 ml) and the layers separated. The toluene extract was dried over sodium sulfate, filtered and the solvent removed in vacuo to yield an oil. Chromatography on silica gel (150 g) eluted with 30% methylene chloride in hexane yielded the title compound as a cream colored solid.

EXAMPLE 2

Preparation of E-3-(4'-Fluoro-3,3',5-trimethyl-[1,1'-biphenyl]-2-yl)-2-propenal (a) E-2-Bromo-4,6-Dimethyl-Cinnamonitrile (2a)

A 5 l, 3-necked round-bottom flask, equipped with an overhead stirrer, thermometer and addition funnel was charged with 2-bromo-4,6-dimethylaniline hydrobromide (713 g, 2.54 mol) and acetone (1.9 l). The slurry was cooled to 15° C. and 48% aqueous hydrobromic acid (450 ml, 4.0 mol), was added. The mixture was cooled to −4° C. then a solution of sodium nitrite (219 g, 3.17 mol) in 400 ml of water was slowly added with vigorous stirring while maintaining an internal temperature of 0° C. Acrylonitrile (550 ml) was charged and the reaction mixture was degassed under vacuum then purged with nitrogen. Cuprous bromide (3.0 g, 0.021 mol) was charged and the mixture stirred with gradual warming to ambient temperature over 6 hours. The mixture was aged with stirring, for 6 additional hours. The mixture was concentrated under vacuum, collecting 3 l of solvent. The residue was diluted with toluene (3 l), the organic extract was washed with 3×500 ml of water, dried over sodium sulfate, filtered, and concentrated to a volume of 1 l. The dark concentrate was charged with triethylamine (1.2 l) and heated at 80°–90° C. under nitrogen for 6.5 hours. The mixture was concentrated under vacuum to a thick slurry then diluted with toluene (2.5 l). The organic phase was extracted 2×500 ml with 3 N aqueous hydrochloric acid, 2×500 ml with water, then dried over sodium sulfate. After filtration the toluene extract was treated with activated charcoal (10 g) at ambient temperature then filtered through super-cel. Removal of the solvent in vacuo yielded a yellow oil which solidified on standing. The crude nitrile was dissolved in a solution of cyclohexane (525 ml) and hexanes (840 ml) with heating. The mixture was gradually cooled to 3° C., filtered, washed with 500 ml of cold hexane and dried in vacuo to yield the Compound 2a as a light yellow solid (mp 95°–96° C.). The crystallization mother liquors contained an additional product.

(b) E-3-(4'-Fluoro-3,3',5-trimethyl-[1,1'-biphenyl]-2-yl)-2-propenoic acid nitrile (2b)

A dry 250-ml, 3-necked round-bottom flask, equipped with a thermometer, addition funnel, and condenser was purged with nitrogen then charged with magnesium turnings (3.5 g, 0.144 mol) and sieve-dried tetrahydrofuran (30 ml, water content:0.02 mg H$_2$O/ml). A solution of 5-bromo-2-fluorotoluene (23 g, 0.122 mol) in 50 ml of tetrahydrofuran was added over 45 minutes maintaining an internal temperature of 40°–50° C. This mixture was allowed to cool to 25° C. over 1 hour. The mixture was filtered into a dry, nitrogen-purged 250-ml round-bottom flask. A 1.33M solution of zinc bromide in tetrahydrofuran (48 ml, 0.064 mol) was added over 10 minutes with stirring while maintaining a temperature between 25°–30° C. A light gray slurry resulted. The aryl zinc slurry was cooled to 25° C. and the Compound 2a (24 g, 0.102 mol) and bis(triphenylphosphine)nickel dichloride (2.0 g, 0.003 mol) are successively charged. The temperature was maintained at 30° C. for 2.5 to 4 hours. Upon verification of completion, the reaction mixture was immediately added to 1.5 molar aqueous hydrochloric acid (200 ml) and extracted with ethyl acetate (100 ml). The organic phase was washed with water (150 ml), dried over sodium sulfate (25–30 g), filtered and concentrated in vacuo to give a dark yellow oil which solidified upon standing. The crude product was dissolved in methylene chloride (50 ml) then applied to a column containing silica gel (70 g) packed in hexane. The column was eluted with 600 ml of methylene chloride to yield the title compound as a yellow solid. HPLC analysis indicates a weight percent purity of 82%. The product was dissolved in hot methanol (50 ml), gradually cooled to ambient temperature and aged overnight with stirring. Crystallization was initiated by seeding at 40° C. The mixture was cooled to −15° C., aged for 30 minutes, and filtered. The crystals are washed with 15 ml of cold (−20° C.) methanol and dried in vacuo to give the Compound 2b as a light yellow solid (mp 86°–87° C.). HPLC analysis indicated a weight percent purity of 99.5%.

(c) E-3-(4'-Fluoro-3,3',5-trimethyl-[1,1'-biphenyl]-2-yl)-2-propenal

A 5-1, 3-necked round-bottom flask, equipped with an overhead stirrer, thermometer and addition funnel was charged with sieve-dried toluene (1.3 l) and the Compound 2b (265 g, 1.0 mol). The mixture was cooled to −45° C. and a solution of diisobutylaluminum hydride (625 ml, 25% solution in toluene) was added over 1 hour, maintaining an internal temperature of −40° C. Upon verification of complete reaction, methanol (50 ml) was carefully added. The reaction mixture was added to a vigorously stirred mixture of 3 N hydrochloric acid (1.5 l) and ice. The mixture was heated at 45° C. for 30 minutes, recooled to ambient temperature and the phases separated. The upper (organic) phase was washed with 3×400 ml of water, dried over sodium sulfate, filtered and concentrated in vacuo to give a yellow-red oil. The crude product was filtered through a column containing silica gel (1.25 kg) eluting with methylene chloride to yield, after concentration, the title compound as a yellow solid (mp 78°–81° C.).

EXAMPLES 3-8

Following the general procedures of Examples 1 and 2, the following compounds of the Formula (IV) are prepared from the appropriate starting material.

| Compound Number | $R_1$ | $R_2$ | $R_4$ | X | Y |
| --- | --- | --- | --- | --- | --- |
| 3 | 3-Cl | 5-Cl | —CN | 4'-F | H |
| 4 | 3-Cl | 5-Cl | —CH=CH—CN | 4'-F | H |
| 5 | 3-CH$_3$ | 5-Cl | —CN | 3'-CH$_3$ | 4'-F |
| 6 | 3-CH$_3$ | 5-Cl | —CH=CH—CN | 3'-CH$_3$ | 4'-F |
| 7 | 3-CH$_3$ | 5-CH$_3$ | —CN | 3'-CH$_3$ | 5'-CH$_3$ |
| 8 | 3-CH$_3$ | 5-CH$_3$ | —CH=CH—CN | 3'-CH$_3$ | 5'-CH$_3$ |

EXAMPLES 9-14

The reduction of the compounds of Examples 3-8 under standard conditions yields the following compounds of the Formulae (II) and (III):

| Compound Number | $R_1$ | $R_2$ | X | Y |
| --- | --- | --- | --- | --- |
| 9 and 10 | 3-Cl | 5-Cl | 4'F | H |
| 10 and 12 | 3-CH$_3$ | 5-Cl | 3'CH$_3$ | 4'F |
| 11 and 14 | 3-CH$_3$ | 5CH$_3$ | 3'CH$_3$ | 5'CH$_3$ |

EXAMPLE 15

Preparation of Methyl E-3-(4'-fluoro-3,3',5-trimethyl-[1,1'-biphenyl]-2-yl)-2-propenoate (a) E-2-bromo-4,6-dimethyl-cinnamate A 250 ml 3-necked, round-bottom flask, equipped with an overhead stirrer, thermometer and addition funnel was charged with 2-bromo-4,6-dimethylaniline hydrobromide (25 g, 0.089 mol), and acetone (66 ml). The slurry was cooled to −4° C. and 48% aqueous hydrobromic acid (15.8 ml) was added. A solution of sodium nitrite (7.6 g) in water (10 ml) was added over 0.5 hour maintaining an internal temperature of 0° C. After 0.25 hour age, methyl acrylate (26.4 ml) was charged and the reaction mixture degassed under vacuum then purged with nitrogen. Cuprous bromide (0.105 g) was added and the mixture stirred at 25° C. for 4 hours. The solvent was removed in vacuo, toluene (100 ml) was charged and the aqueous phase removed. The toluene extract was washed with water (2×30 ml), dried over sodium sulfate, filtered and concentrated in vacuo to give a yellow oil. Tri-n-butylamine (52 ml) was charged and the mixture heated at 120°–125° C. for 12 hours. The reaction was monitored by thin layer chromatography (tlc) (silica gel plates, eluting with 5% ethyl acetate in hexane). The mixture was poured into ice water (100 ml) and acidified with 3 M aqueous hydrochloric acid then extracted with toluene. The toluene extract was washed with 3 M aqueous hydrochloric acid, water, dried over sodium sulfate, filtered, and concentrated in vacuo to give a dark yellow oil. Chromatography on silica gel (200 g), eluted with 5% ethyl acetate in hexane yielded the title compound as a light yellow liquid. NMR 60 (60 MHz, CDCl$_3$, δ): 7.60 (d, 1H, J=16 Hz), 7.20 (bs, 1H), 6.80 (bs, 1H), 6.00 (d, 1H, J=16 Hz), 3.71 (s, 3H), 2.28 (s, 3H), 2.22 (s, 3H).

(b) Methyl E-3-(4'-Fluoro-3,3'-5-trimethyl-[1,1'-biphenyl]-2-yl)-2-propenoate

A dry 50 ml round bottom flask was charged with magnesium turnings (0.916 g, 38.1 mmol) and sieve-dried tetrahydrofuran (15 ml). A solution of 5-bromo-2-fluorotoluene (4.5 g, 23,8 mmol) in tetrahydrofuran (10 ml) was added over 15 minutes maintaining an internal temperature of 45° C. The resulting solution was transferred to a dry 50 ml round bottom flask containing freshly fused zinc chloride (2.0 g, 14.9 mmol) and aged with stirring for 0.5 hour at 25° C. After mixture was cooled to −5° C., Compound 15a (5.0 g, 18.58 mmol) and bis(triphenylphosphine) nickel dichloride (0.607 g, 0.9 mmol) were charged and the mixture heated at 20°–25° C. for 12 hours, at which time complete disappearance of Compound 15a was evident from HPLC analysis. The mixture was diluted with cold 3 M aqueous hydrochloric acid and extracted with ethyl acetate. The ethyl acetate extract was washed with water, dried over magnesium sulfate, filtered and concentrated in vacuo to yield a yellow oil. Chromatographic purification on a silica gel column (100 g) eluted with 1.6 l of hexane and 1.6 l of 30% methylene chloride in hexane yielded the title compound as a yellow oil. NMR (60 MHz, CDCl$_3$,δ), 7.50 (d, 1H, J=15 Hz), R 7.25–7.00

(bm, 5H), 5.65 (d, 1H, J=15 Hz), 3.60 (s, 3H), 2.35 (s, 3H), 3.25 (bs, 6H).

What is claimed is:

1. A process for the preparation of a compound represented by the following general Formula (IV)

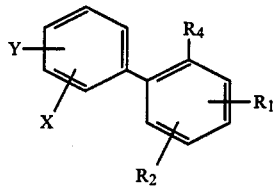
(IV)

wherein:
R₁ and R₂ independently re:
  (1) chloro;
  (2) fluoro; or
  (3) $C_{1-4}$ alkyl;
R₄ is
  (1) —CH=CHCN;
  (2) —CH=CHCO₂R₅; or
  (3) —CH=CHCH (OR₅)₂,
in which R₅ is $C_{1-4}$ alkyl; and
X and Y independently are:
  (1) hydrogen;
  (2) chloro;
  (3) fluoro;
  (4) $C_{1-4}$ alkyl; or
  (5) $C_{1-4}$ alkoxy;
which comprises reacting a compound of the Formula (V):

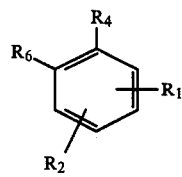
(V)

wherein R₁, R₂ and R₄ are defined above; and R₆ is halogen with a compound of the Formula (VI)

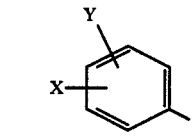
(VI)

wherein X and Y are defined above and R₇ is
  (1) ZnR₈;
  (2) MgR₈;
  (3) CdR₈; or
  (4) Li
in which R₈ is halogen or a radical represented by the following formula:

wherein X and Y are defined above, in the presence of a nickel catalyst.

2. A process according to claim 1 for the preparation of a compound represented by the Formula (IV) wherein:
R₁ and R₂ independently are chloro, fluoro or methyl and are in the 3- and 5-position respectively; and
X and Y independently are chloro, fluoro, methyl or methoxy.

3. A process according to claim 2 wherein:
R₁ is 3-methyl;
R₂ is 5-methyl;
X is 3'-methyl; and
Y is 4'-fluoro.

4. A process according to claim 1 wherein the nickel-catalyst is an organophosphine coordinated nickel dihalide complex.

5. A process according to claim 4 wherein the nickel-catalyst is bis(triphenylphosphine)nickel dichloride.

6. A process according to claim 1 wherein the compound of the Formula (VI) is the compound in which R₇ is ZnR₈.

7. A process according to claim 1 wherein the process is conducted between 10 and 65° C. in an inert solvent.

* * * * *